(12) United States Patent
Jackson et al.

(10) Patent No.: US 7,221,972 B2
(45) Date of Patent: May 22, 2007

(54) ULTRASOUND SYSTEM WITH PROTOCOL-DRIVEN USER INTERFACE

(75) Inventors: John I. Jackson, Menlo Park, CA (US); Lewis J. Thomas, Palo Alto, CA (US); Cynthia L. Kerby, Carnation, WA (US); Laurence S. McCabe, Sunnyvale, CA (US); David R. DeWitt, Livermore, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 319 days.

(21) Appl. No.: 10/892,921

(22) Filed: Jul. 16, 2004

(65) Prior Publication Data

US 2005/0049506 A1 Mar. 3, 2005

Related U.S. Application Data

(63) Continuation-in-part of application No. 10/651,374, filed on Aug. 29, 2003, now Pat. No. 6,953,433.

(51) Int. Cl.
*A61B 5/05* (2006.01)
*A61B 8/00* (2006.01)

(52) U.S. Cl. .................. 600/407; 600/443 A
(58) Field of Classification Search ............ 600/407, 600/410, 425, 430, 437, 443–447, 454–456, 600/458
See application file for complete search history.

(56) References Cited

U.S. PATENT DOCUMENTS

| | | | |
|---|---|---|---|
| 4,796,634 A * | 1/1989 | Huntsman et al. | 600/457 |
| 5,544,654 A * | 8/1996 | Murphy et al. | 600/443 |
| 5,831,612 A | 11/1998 | Stoval et al. | |
| 6,139,498 A | 10/2000 | Katsman et al. | |
| 6,141,398 A | 10/2000 | He et al. | |
| 6,148,095 A * | 11/2000 | Prause et al. | 382/131 |
| 6,275,869 B1 | 8/2001 | Sieffert et al. | |
| 6,397,098 B1 | 5/2002 | Uber et al. | |
| 6,458,081 B1 | 10/2002 | Matsui et al. | |
| 6,488,629 B1 * | 12/2002 | Saetre et al. | 600/443 |
| 6,641,538 B2 * | 11/2003 | Nakaya et al. | 600/458 |
| 6,773,398 B2 | 8/2004 | Ogasawara et al. | |

(Continued)

OTHER PUBLICATIONS

Acuson Sequoia 512 Ultrasound System, User Manual, cover page, pp. ii, 184, and 186-189 (Apr. 1999).

(Continued)

*Primary Examiner*—Francis J. Jaworski

(57) ABSTRACT

The embodiments described herein relate to stepping through the stages of a protocol using an input device and a protocol controller for a medical diagnostic imaging system. The protocol controller may be operative to transition from one stage to a next stage in the protocol in response to no more than a single input from the input device. Thus, a single input from the input device may indicate to the protocol controller to transition to each of the stages of the protocol. In one embodiment, the same single input, such as a stage transition input, is received to transition to each stage of the at least two sequential stages. In another embodiment, different single input, such as different keys on a keyboard, may be used to transition to different stages of the at least two sequential stages. Other embodiments are provided, and each of the embodiments described herein can be used alone or in combination with one another.

23 Claims, 4 Drawing Sheets

U.S. PATENT DOCUMENTS

| | | | |
|---|---|---|---|
| 6,786,869 B2 | 9/2004 | Hashimoto | |
| 6,953,433 B2 * | 10/2005 | Kerby et al. | 600/443 |
| 2002/0035326 A1 | 3/2002 | Kamiyama | |
| 2003/0191389 A1 | 10/2003 | Sano et al. | |

OTHER PUBLICATIONS

Acuson Sequoia 512 Ultrasound System, Administrator Manual, cover page, pp. ii-iii, and 39-47 (Apr. 1999).

"Megas GP—Advanced Applications—Image Management System (I.M.S.)," http://www.esaote.com/products/ultrasound/megas/cAdvApplicImsGP.htm, 1 page (printed Oct. 29, 2002).

"Ultrasound Vivid FiVe," GE Medical Systems, http://www.gemedicalsystems.com/rad/us/products/vivid_5/msuvivid5.html, 2 pages (printed Oct. 29, 2002).

"HP Introduced Advanced Diagnostics for HP SONOS 5500 Echocardiography Ultrasound System," http://www.pacificwestmedical.com/hewlett_packard.htm, 5 pages (printed Oct. 29, 2002).

"Sonos 5500—Ultraperformance Upgrade," Philips Medical Systems, http://www.medical.philips.com/main/products/ultrasound/cardiology/sonos5500/upgrades, 2 pages (printed Jul. 30, 2003).

"Sonos 5500" Philips Medical Systems, http://www.medical.philips.com/main/products/ultrasound/cardiology/sonos5500/, 1 page (printed Sep. 3, 2004).

"Sonos 5500—Features and Benefits," Philips Medical Systems, http://www.medical.philips.com/main/products/ultrasound/cardiology/sonos5500/features, 1 page (printed Jul. 30, 2003).

"Annex X: Ultrasound Staged Protocol Data Management," 3 pages (undated).

* cited by examiner

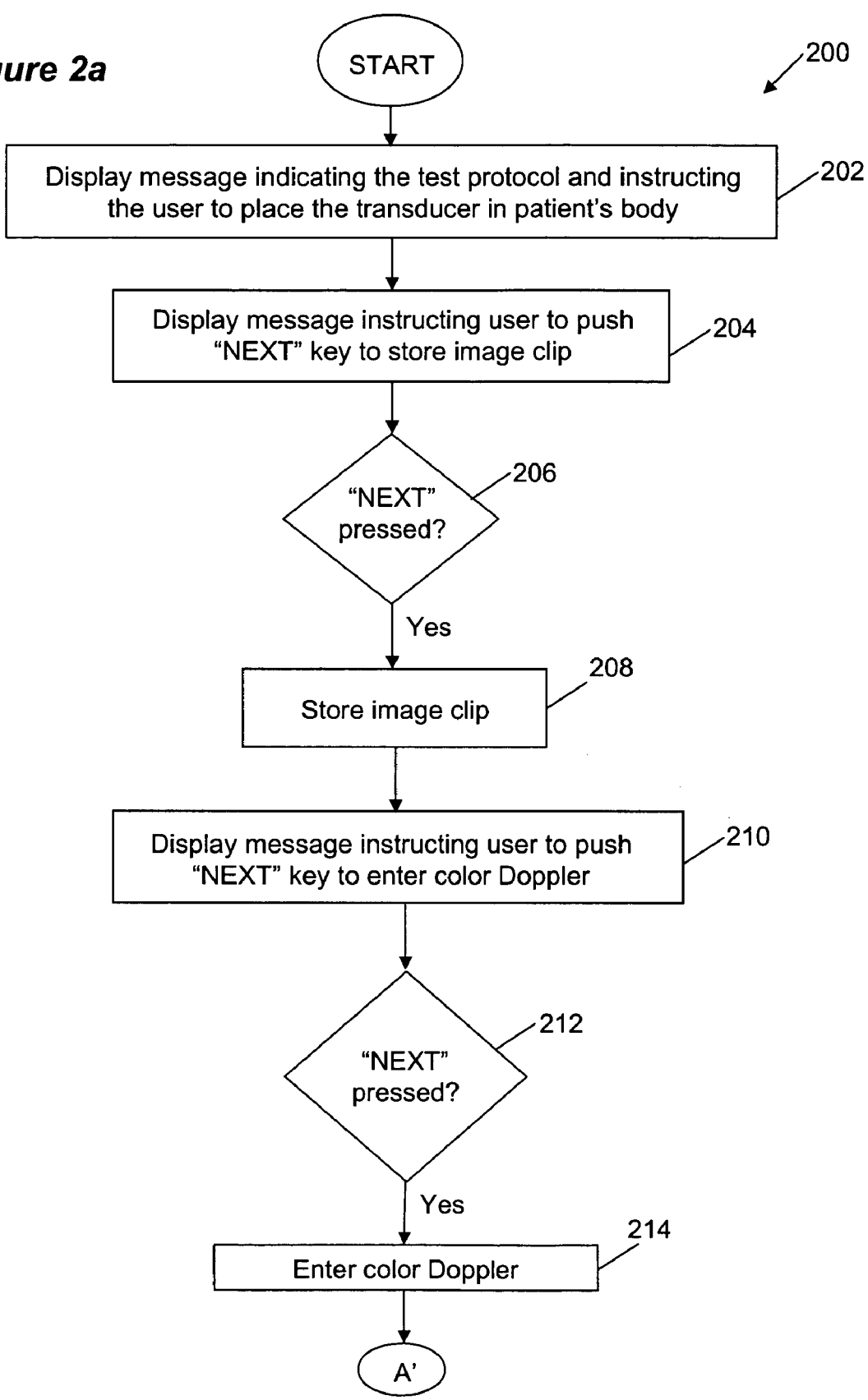

ULTRASOUND SYSTEM WITH PROTOCOL-DRIVEN USER INTERFACE

REFERENCE TO RELATED APPLICATIONS

This application is a continuation-in-part of U.S. patent application Ser. No. 10/651,374 filed on Aug. 29, 2003 now U.S. Pat. No. 6,953,433, which is incorporated by reference herein in its entirety.

BACKGROUND

Many ultrasound exams are driven by a rigid protocol. The system operator acquires standard views in a fixed order, entering different modes (color Doppler, PW, CW, M-mode) in a specific order, making specific measurements in a specific order, and saving appropriate images and video clips.

One example of a protocol is a cardiology exam, such as a stress echo examination. The common practice is to step the user through a pre-defined series of clip acquisitions that allow the clinician to compare left ventricular motion from a variety of views, with and without stressing the heart. Within the industry, there are standard pre-defined protocols (e.g., two-stage exercise stress, four-stage exercise stress, etc.). The ACUSON Sequoia™ echocardiography platform offers some degree of user customization of protocol factors such as the number of stages, the number of views, and the clip capture parameters used for each stage/view.

Operating the ultrasound system to step through the protocol properly may be difficult. Typically, the ultrasound system includes a keyboard with many keys that requires complex input to step through the protocol. This complexity limits those who may operate the system properly. Specifically, the operator of the ultrasound system must be familiar with the ultrasound system in order to manipulate the ultrasound system to follow the prescribed protocol and acquire the appropriate clinical data. Moreover, this complexity may increase the possibility that the protocol is incorrectly followed. Even for an experienced ultrasound system operator, the complex input may increase the number of errors in stepping through the protocol. Thus, this complexity in running the protocol operating the ultrasound system may limit the usability and reduce the reliability of the ultrasound system.

SUMMARY

The present invention is defined by the following claims, and nothing in this section should be taken as a limitation on those claims.

By way of introduction, the embodiments described below relate to stepping through the stages of a protocol using an input device and a protocol controller for a medical diagnostic imaging system. The protocol controller may be operative to transition from one stage to a next stage in the protocol in response to no more than a single input from the input device. Thus, a single input from the input device may indicate to the protocol controller to transition to each of the stages of the protocol.

In one embodiment, the same single input, such as a stage transition input, is received to transition to each stage of the at least two sequential stages. Examples of a stage transition input may include a dedicated key on a keyboard, a voice input, a foot-pedal input, or a key or button on the ultrasound transducer. The protocol controller may receive a signal from the input device indicating that the stage transition input has been activated. The protocol controller may then execute the transition to the next sequential stage of the protocol. In this manner, the stage transition input indicates to the protocol controller when to execute the stages of the protocol. Rather than the protocol controller requiring complex input to transition through the stages of the protocol, the stage transition input enables a simpler manner (such as by the press of a single button) in which to indicate to the protocol controller to transition through the next stage of the protocol.

In another embodiment, different single input, such as different keys on a keyboard, may be used to transition to different stages of the at least two sequential stages. Other embodiments are provided, and each of the embodiments described herein can be used alone or in combination with one another.

The embodiments will now be described with reference to the attached drawings.

BRIEF DESCRIPTION OF THE DRAWINGS

FIGS. 2a–c are a flow diagram illustrating transitioning through an exemplary protocol.

DETAILED DESCRIPTION OF THE PRESENTLY PREFERRED EMBODIMENTS

Figure 1:
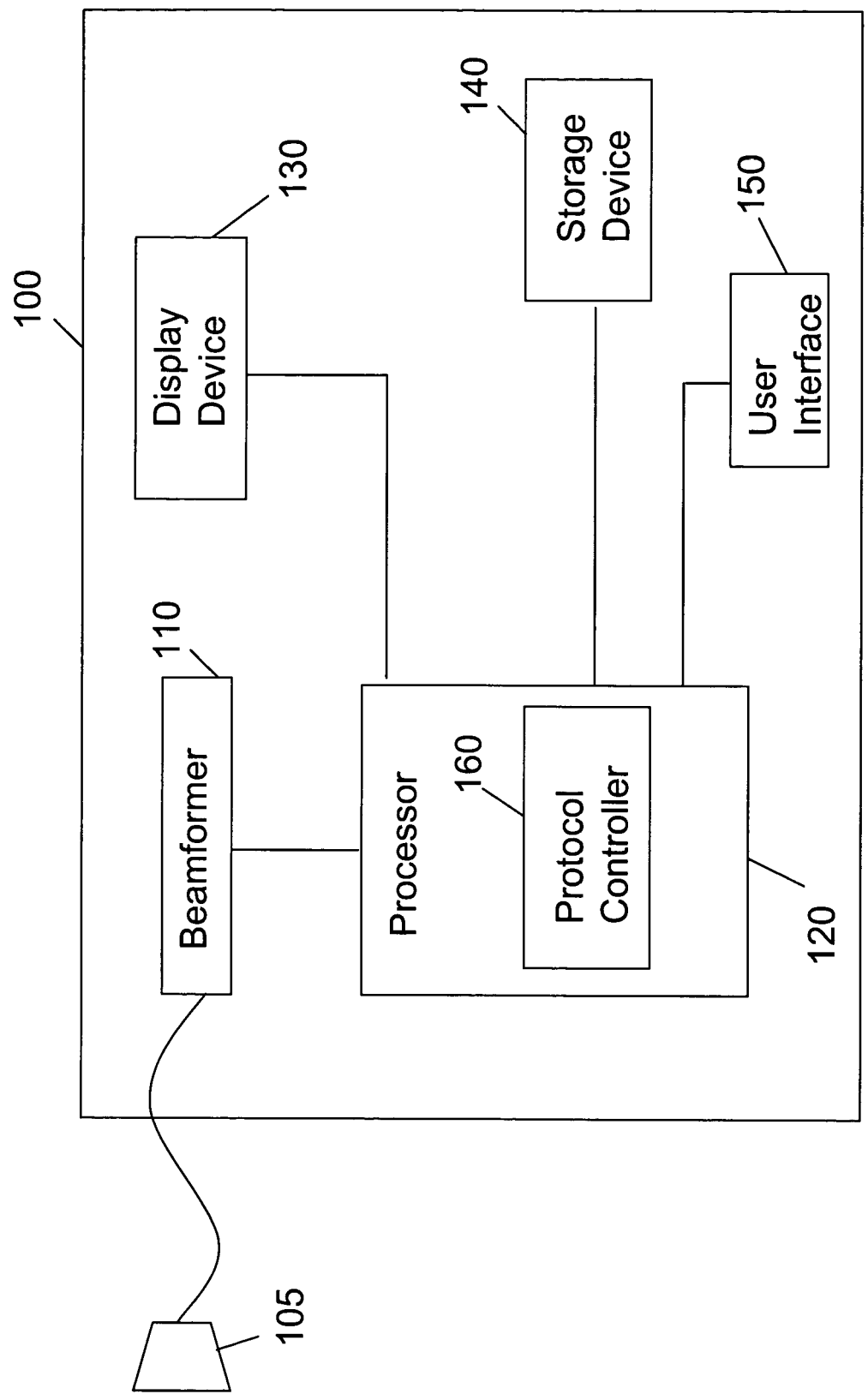
FIG. 1 is a block diagram of a medical diagnostic ultrasound imaging system of an embodiment.

By way of introduction, the embodiments described below relate generally to protocols used in a medical diagnostic imaging system. Although any type of imaging system can be used, these embodiments will be illustrated in conjunction with an ultrasound imaging system. Turning now to FIG. 1, an ultrasound system 100 typically comprises a transducer probe 105, a beamformer 110, a processor 120, a display device 130, a storage device 140, and a user interface 150. The term "processor" is being used to broadly refer to the hardware components and/or software components (i.e., computer-readable program code) of the ultrasound system 100 that are used to implement the functionality described herein. For example, user interface 150 may enable the user to enter commands and/or information to be sent to processor 120. User interface 150 may comprise any one or any combination of the following: a keyboard, a mouse, a joystick, a microphone, a footswitch, or the like. When the user activates a key on the keyboard, for example, a signal is sent to the processor indicating that a key has been activated. User interface may also enable the user to receive data from processor 160. For example, visual data from processor 160 may be displayed on a monitor 36, or other type of display device. Further, aural data from processor 160 may be output using speakers or other audible output devices.

During an ultrasound examination, a sonographer contacts the transducer probe 105 with a patient, and the ultrasound system 100 generates an ultrasound image. In general, the ultrasound system's processor 120 causes the beamformer 110 to apply a voltage to the transducer 105 to cause it to vibrate and emit an ultrasonic beam into the portion of the patient's body in contact with the transducer 105. Ultrasonic energy reflected from the patient's body impinges on the transducer 105, and the resulting voltages created by the transducer 105 are received by the beamformer 110. The processor 120 processes the sensed voltages to create an ultrasound image that is displayed on the display device 130.

The ultrasound system 100 can be used to perform any number of exams (or "studies") of a patient. Some studies require a user to follow a defined "protocol." A "protocol" is a sequence of steps performed by a user (e.g., a sonographer or physician) to perform a particular ultrasound study. A protocol is often used with a "staged" study, although a protocol can also be used with a non-staged study. A staged study contains a set of images acquired under specified conditions during two or more time intervals called "stages" with a consistent set of images called "views" acquired during each stage of the study. The protocol for a staged study dictates the actions a user preferably performs to complete the study. A user proceeds through a staged protocol exam one stage at a time, acquiring images with the capture settings of each stage. One example of a staged study is a stress echo ultrasound study, which allows a clinician to compare left ventricular motion from a variety of views, with and without stressing the heart. A typical stress echo protocol consists of the user imaging and capturing clips of the patient's heart while the patient's heart is at its resting heart rate. The standard views of the heart that are imaged and captured are Parasternal Long Axis (PLAX), Parasternal Short Axis (PSAX), Apical Four Chamber (A4C), and Apical Two Chamber (A2C). Next, the patient's heart rate is increased to its maximum, either by exercise (e.g., treadmill, bicycle) or with the use of drugs (for those patients who are unable to exercise). The user will image and capture clips (standard views) of the patient's heart while the patient's heart rate is at its maximum increase, before the heart rate slows down (images are typically captured within 60–90 seconds after exercise has stopped). The user reviews the captured clips and selects the clips he wants to keep. The rest of the clips are deleted when the study has ended. The standard has been to capture at least four clips of each view and only keep the best clip for each view of each stage. Another example of a protocol is an A4C view, which is discussed below regarding FIGS. 2*a*–*c*.

In order to execute the various stages of a protocol, the user preferably operates user interface 150 of the ultrasound system 100. In a system which has a keyboard as part of user interface 150, the user may be required to enter a complex sequence of multiple keys in order to execute one stage of the protocol and transition to the next stage in the protocol. This requirement to enter multiple keys limits those who may be able to follow the protocol correctly on ultrasound system 100. Specifically, a user should be experienced both generally with the ultrasound system 100 and also specifically with the protocol in order to step through the protocol properly. This experience level may bar others with lesser experience from being able to execute a protocol. For example, a new user of ultrasound system 100, such as a resident performing an exam during the off-hours or a sonographer who is asked to complete a complex research protocol, may not be able to operate ultrasound system 100 to execute the protocol properly.

One aspect of the preferred embodiments is to simplify the transition between the multiple stages of a protocol. In one embodiment, one input from the user via user interface 150 allows the user to transition from one stage in the protocol to the next stage in the protocol. The one input from the user may comprise a press of a single key, a press of a pushbutton, a press of a footswitch, a vocal input (e.g., a specific vocal command such as "NEXT"), or the like. In the context of pressing a single key, the single key may be a key dedicated to transitioning from one step to the next in the protocol. For example, the key on the keyboard may always be dedicated to transitioning from one step to the next in the protocol during any operation of ultrasound system 100. As described below with respect to FIGS. 2*a*–*c*, a "NEXT" key is used to transition. The keyboard may have such a "NEXT" key which during any operation of ultrasound system 100 will be interpreted as a request for transition. As another example, the key may be dedicated only during the operation of the protocol on ultrasound system 100. Specifically, one of the keys on the keyboard (such as the ESC key) may be assigned to be the key to indicate transitioning of the protocol only during operation of the protocol.

Alternatively, the single key may be any key which is available for use on the keyboard. For example, the protocol controller may designate that the press of any single key may signal transition to the next stage in the protocol. As another example, the protocol controller may designate that different keys should be pressed to transition the stages within the protocol. Specifically, when transitioning to the first stage of the protocol, the "1" key may be pressed, when transitioning to the second stage of the protocol, the "2" key may be pressed, and so on. Further, rather than using a key (such as a dedicated key) to transition through the protocol, an icon on the display may be used. In this embodiment, an ultrasound system may provide an icon that represents an automated sequence of exam measurement. The icon may display the name of the currently active measurement and a tool tip that displays the next measurement in the sequence. When the user clicks on the icon, the user interface 150 may send a signal to the protocol controller 160 indicating a request to transition to the next stage in the protocol. The input from user interface 150 may be sent as a signal to the protocol controller 160 indicating the single input. The protocol controller 160 may then transition to the next stage in the protocol. Moreover, the protocol controller 160 may execute the next stage in the protocol, as discussed in more detail below.

This type of single input transitioning through the multiple stages of the protocol simplifies the operation of ultrasound system 100. Rather than multiple input required to transition, a single push of a button, for example, may be used. Moreover, the single input transitioning is particularly beneficial with ultrasound technologies such as TEQ and Doppler TEQ, which address image optimization issues that cannot be easily predicted. These ultrasound technologies may require additional input, other than the single input, from the user. Because the transitioning between the stages of the protocol is greatly simplified, other steps in the protocol which may require more input become more predictable. In this manner, the operation of stepping through the multiple stages of a protocol is simplified and allows even an inexperienced user to operate ultrasound system 100. Further, during operation of the protocol, the processor 120 may provide data, either visual or aural, to the user via user interface 150 which describes the current and/or next steps.

The single input enables the protocol controller 160 to transition from one step to the next in the protocol by a single input and automatically control various system parameters in accordance with the protocol to guide the user through a pre-defined series of clip acquisitions. For example, an ultrasound system can be programmed with a series of preset, defined protocols (e.g., a two-stage exercise stress echo protocol, a four-stage exercise stress echo protocol, etc.) that a user can select for a particular study. The protocol may include a series of steps that should be executed in a sequential order. Based on the selected protocol, the ultrasound system automatically moves through stages and views, moves between imaging and review of captured images, provides automatic movement to the next stage, and performs automatic storage and retrieval of each view. The ultrasound system would also know how to capture and playback clips and can automate system actions where appropriate, such as automatically performing a system transition, to help eliminate the number of steps (i.e., button hits) the user must perform, thereby reducing the user's workload.

Further, the protocol may include a series of steps operated in a sequence. As discussed above, the single input may execute the series of steps sequentially. Alternatively, the protocol may include different steps to execute, such as different branches. For example, the protocol may include several branches. A branch to the protocol may be executed based on the ultrasound data gathered during a previous executed stage in the protocol. In this example, if the protocol determines that a specific branch should be executed (e.g., the ultrasound data is analyzed to determine that the specific branch should be executed), upon receiving the single input, the first step in the specific branch may be executed. In this manner, even if a protocol includes a complicated tree of steps, proceeding through the branches of the tree of steps may be simplified by using the single input to step through the protocol.

The protocol controller 160 may be implemented as a software-implemented finite state machine. Of course, other implementations can be used. Finite state machines are known in the art and are described in, for example, chapter 5 of "Dynamic Modeling in Object-Oriented Modeling and Design" by Rumbaugh, Blaha, Premerlani, Eddy and Lorensen, which is hereby incorporated by reference. It is preferred that the finite state machine design pattern be implemented in such a way that the finite state machine software allows the protocol controller 160 to implement a state model diagram in a highly configurable way. A state model diagram relates events and states. When an event is received, the next state depends on the current state as well as the event. One such event is a single input from user interface 150.

A change of state caused by an event is called a transition. A state model diagram is a graph whose nodes are states and whose directed arcs are transitions labeled with event names. There can be guards and actions associated with state transitions, as well as state entry and state exit actions. The finite state machine represents a collection of hierarchical states, where only one sub-state is current at any time. An application can have multiple states by having multiple finite state machines. The state model diagram of a given protocol is used to initiate the execution of the application functionality. It is driven by events, which are due to user actions. There can be concurrent finite state machines active at the same time, and they can communicate by sending messages, which may cause state transitions and actions to be executed. The finite state machine model definition is defined in a file using a state model meta-language. This allows a concise definition of all the information represented in the state model diagram. No software coding is required to define the states or their relationships and transitions of the state model diagram. The states and some of their relationships and transitions can be changed without having to recompile and re-build the software.

Each protocol has its own set of parameters that are defined by the protocol and get initialized when the protocol finite state machine is created and initialized. The parameters define to the system how to perform or respond to certain user actions (e.g., selections). The protocol finite state machine knows what state the protocol is in and defines the sequences of operations that occur in response to external stimuli (e.g., user actions, such as button presses or selections). The external stimuli (user actions) generate system events, and the finite state machine's response to an event depends on the state of the finite state machine receiving the event. It can include a change of state or the sending of another event. The protocol controller 160 can have one or more protocol finite state machines created and running concurrently. The protocol finite state machines can send events to each other, so they can be synchronized.

Figure 2B:
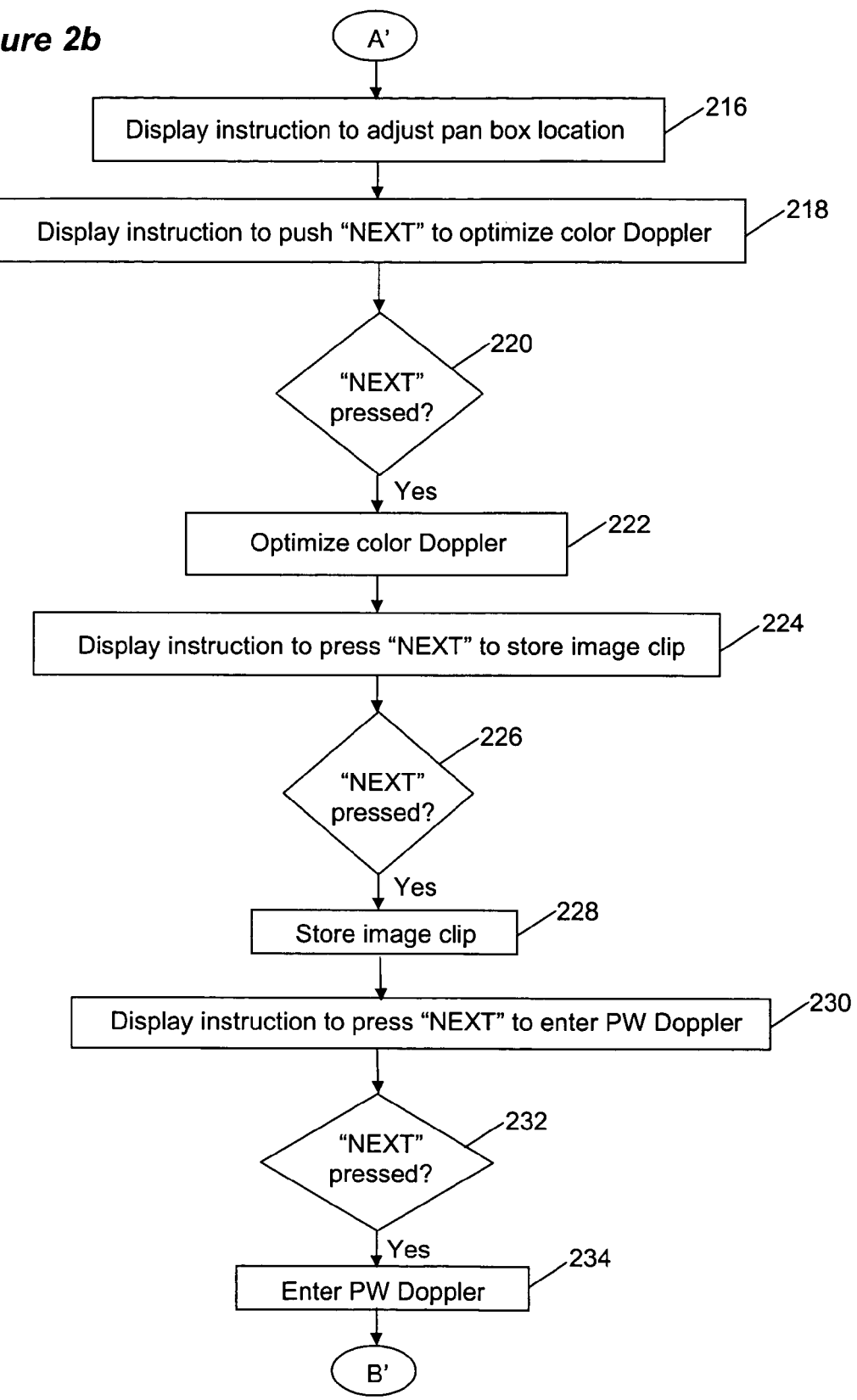
Figure 2C:
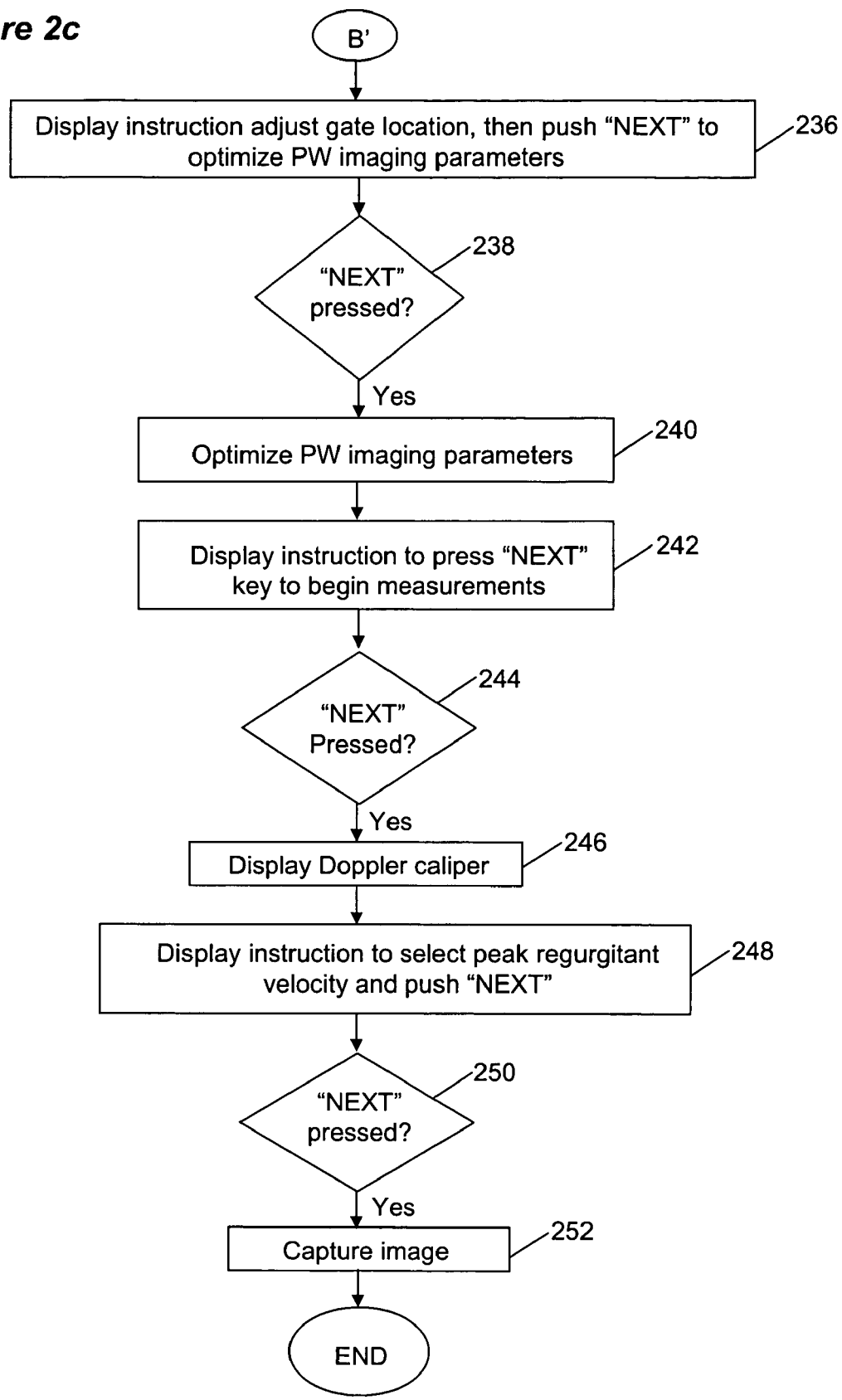

FIGS. 2a–c are a flow diagram 200 of one example of transitioning through the multiple stages of an exemplary protocol for an "A4C View." Upon starting the protocol, the processor 120 may send a message to the display of user interface 150 to display a message indicating the particular test protocol and instructing the user to place the transducer in the appropriate place on the patient's body, as shown at block 202. An additional message may be displayed instructing the user to push the "NEXT" key to store the image clip, as shown at block 204. As discussed above, one aspect of the preferred embodiments is simplifying the transitioning between the multiple stages in a protocol. The user may enter a single input, such as a single key press, in order to transition to the next stage of the protocol. Further, in the case of a single key press, the keyboard may have a single key which is dedicated to the transitioning to the next stage. As shown in the flow diagram in FIGS. 2a–c, the dedicated key may be a "NEXT" key.

The protocol controller 160 may then wait until the "NEXT" key is pressed, as shown at block 206. When pressed, the protocol controller may store the image clip, as shown at block 208. Further, the protocol controller 160 may display a message instructing the user to press the "NEXT" key to enter color Doppler, as shown at block 210. Color Doppler is a mode of the ultrasound system 100 whereby the system acquires information at multiple times. The acquired data may be manipulated to display different velocities in the image using different colors. The protocol controller 160 may then wait until the "NEXT" key is pressed, as shown at block 212. When pressed, the protocol controller may enter color Doppler, as shown at block 214.

The protocol controller 160 may display an instruction to the user to adjust the pan box location, as shown at block 216. The user may focus on a portion of the image displayed on the screen by adjusting the pan box location. Typically, the user may use a trackball, which may be a part of user interface 150, in order to focus on a portion of the image, such as a certain quadrant of the image.

The protocol controller 160 may further display a message instructing the user to press the "NEXT" key to optimize the color Doppler imaging parameters, as shown at block 218. The parameters to optimize color Doppler imaging may include gain and scale. The protocol controller 160 may then wait until the "NEXT" key is pressed, as shown at block 220. When pressed, the protocol controller may optimize color Doppler, as shown at block 222. The protocol controller 160 may display a message instructing the user to press the "NEXT" key to store an image clip, as shown at block 224. The protocol controller 160 may then wait until the "NEXT" key is pressed, as shown at block 226. For example, when the user is satisfied with the image presented on the display, the user may press the "NEXT" key to store the image clip, as shown at block 228. As discussed in more detail below, the protocol may automatically transition to store the image clip after the user presses the "NEXT" key.

The protocol controller 160 may display a message instructing the user to press the "NEXT" key to enter PW Doppler, as shown at block 230. PW Doppler is pulsed wave Doppler which determines velocity information for one localized region. The protocol controller 160 may then wait until the "NEXT" key is pressed, as shown at block 232. After the user presses the "NEXT" key, the protocol controller 160 may transition to the next step and enter PW Doppler, as shown at block 234.

The protocol controller 160 may display a message instructing the user to adjust gate location and press the "NEXT" key to optimize PW imaging parameters, as shown at block 236. The protocol controller 160 may then wait until the "NEXT" key is pressed, as shown at block 238. After the user presses the "NEXT" key, the protocol controller 160 may optimize PW imaging parameters, as shown at block 240.

The protocol controller 160 may display a message instructing the user to press the "NEXT" key to begin measurements, as shown at block 242. The protocol controller 160 may then wait until the "NEXT" key is pressed, as shown at block 244. After the user presses the "NEXT" key, the protocol controller 160 may display the Doppler caliper, as shown at block 246. The protocol controller 160 may display a message instructing the user to select peak regurgitant velocity and press the "NEXT", as shown at block 248. The protocol controller 160 may then wait until the "NEXT" key is pressed, as shown at block 250. After the user presses the "NEXT" key, the protocol controller 160 may capture the image, as shown at block 252.

The protocol controller 160 allows for the user to diverge from the protocol at any point. The user may thereafter reenter the protocol where it was left, or reenter at any other point in the protocol. Moreover, the protocol controller facilitates the automatic labeling of images. For example, the first clip which is captured in block 208 may be labeled as a B-mode, A4C view. As another example, the second clip which is captured in block 228 may be labeled as a color Doppler A4C view of the mitral valve. As still another example, the next still image may be labeled as a PW of the mitral valve, etc.

As discussed above, the protocol controller 160 may execute commands in the stages of the protocol. In order to execute a command, the protocol controller 160 may use a "macro." In software, the term "macro" is often used to describe a segment, script, or skeleton that can be used by another process, preferably repeatedly and in more than one way. For example, in Excel (Microsoft Corporation, Redmond, Wash.), one can build a macro (preferably in Visual C) to perform a sequence of instructions. Once built, the macro can be used repeatedly with a given spreadsheet or moved easily to another spreadsheet and be used there, potentially in a significantly different context. Accordingly, the term "macro" means any sequence of instructions that can be interpreted by another process, causing that process to execute or have executed a sequence of instructions. Macros can be exceedingly useful as building blocks for the protocol controller 160. A macro may be a set of parameter definitions that define specific ultrasound system behavior. Each macro (or set of parameters) can be used as ultrasound preset data values or ultrasound system controlling parameters. Every protocol will consist of some set of macros. Once a macro has been defined, it belongs to a pool of defined macros. A new protocol can be created by combining a unique set of macros from this pool of already-defined macros. The protocol controller 160 itself can then be implemented as an engine used to drive a series of macros.

Instead of being a set of parameters, a macro can be a code snippet. That is, a macro can be any sequence of instructions that can be interpreted by another process, causing that process to execute a sequence of instructions. In this sense, a "macro" is any sequence of instructions that can be interpreted by another process, causing that process to execute or have executed a sequence of instructions. For example, a protocol can have a data or image capture segment. Each instantiation of capture can be built as a macro, such as "store image to disk" or "store clip to VCR." Of particular usefulness might be an instantiation of a macro for storing data utilizing parameters for a data type and device type: Store <datatype> to <devicetype>. In this way, each segment of the protocol can be written as a macro utilizing parameter. The protocol itself can then be implemented as an engine used to drive a series of macros. This development is particularly useful in that the engine (i.e., the protocol controller 160) can be interrupted after execution of a macro, the sequence can be marked to indicate where to re-enter, and the user can run another sequence of macros (protocol) before returning to the exit point and continuing execution of the original protocol.

As mentioned above, the collection of macros controls one or more of the following: imaging system settings, the user interface, a display area, and a system peripheral. More specifically, the macros can control one or more of the following: transmit parameters and settings, receive parameters and settings, imaging mode, imaging parameters and settings, filters and processing specifics, signal processing options, post-processing options, frequency, harmonic, mode, pulse repetition frequency, frame-rate, display control, number of views, annotation, a user interface page displayed in the display area, an active tool displayed in the display area, a cursor in the display area, a number of views in the display area, system control, measurements and reports, annotations, pictograms, review and display features, user preferences, which user interface page is displayed, and which tool/cursor is active, a DICOM device, a CD, a DVD, a VCR, an MO drive, a printer, and a networked device.

Suitable protocol macros may include a clip capture macro, a clip playback macro, a workflow macro, and an acquisition sequence macro. The following are examples of these types of macros:

Clip Capture

Number of clips to capture per clip capture activation (1, 2, 4, etc).

Duration/length of each clip to be captured (in seconds, microseconds, heartbeats, etc).

R-wave trigger clip capture enabled/disabled (capture clips based on patients heartbeat or not).

Clip capture delay time (a delay time after an r-wave trigger occurs to start capturing the clip, in microseconds).

Clip compression level.

Clip capture size (full screen, quarter screen, or some other derivative size).

Clip Playback

Clip playback speed.

Clip playback mode (align heartbeats of multiple captured clips or just play each clip or start each clip together at the same time).

Workflow

Enable/disable to automatically delete unselected clips at end of exam.

Enable/disable to automatically move the system to the next stage of a staged protocol.

Enable/disable to automatically start and stop VCR recording based upon some defined event.

Enable/disable to automatically save and recall imaging parameters (a defined set such as transmit/receive settings, imaging mode, filters and processing settings, etc.) upon some defined event such as the first view of each stage of a staged protocol, or at the beginning of a defined acquisition sequence, etc.).

Enable/disable to automatically transfer specifically defined types of data to specifically defined devices or locations, such as transfer clips over the network at the end of each clip capture, transfer still images to a CD at the end of exam, etc.

Enable/disable annotations or pictograms upon the occurrence of some user or system event.

Enable/disable automatically performing a specific measurement upon the occurrence of some user or system event.

Enable/disable entry into a specific measurement and/or report package upon the occurrence of some user or system event.

Enable/disable system guidance, such as a guidance to the user on the next step to perform for a specific type of exam.

Enable/disable to automatically change the imaging mode based upon the occurrence of some user or system event.

Acquisition Sequence

Define a set of imaging acquisition steps where each step would have varying imaging acquisition parameter definitions, the system could automatically move through the acquisition steps or could move through the acquisition steps based upon the occurrence of some user/system event.

As noted above, each of the embodiments described herein can be used alone or in combination with one another. As also noted above, these embodiments can be used with image modalities other than ultrasound imaging, and the claims should not be limited to any particular type of image modality unless explicitly recited therein. Examples of different types of image modalities that can be used with these embodiments include, but are not limited to, computed tomography (CT), magnetic resonance imaging (MRI), computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy.

It is intended that the foregoing detailed description be understood as an illustration of selected forms that the invention can take and not as a definition of the invention. It is only the following claims, including all equivalents, that are intended to define the scope of this invention.

What is claimed is:

1. A medical diagnostic imaging system comprising:
   a storage device storing a protocol for performing a medical diagnostic procedure on the medical diagnostic imaging system, the protocol partitioned into at least a first stage and a second stage, the stages being different from one another;
   an input device;
   a protocol controller operative to transition to the first stage in response to no more than a first single input from the input device and transition from the first stage to the second stage in the protocol in response to no more than a second single input from the input device, the protocol controller operative to configure the medical diagnostic imaging system for the first stage and the second stage in the protocol; and
   a display controller operative to display a message prior to the protocol controller configuring the medical diagnostic imaging system for each of the first and second stages in the protocol, the message comprising an instruction for an operator to perform in advance of each of the first and second stages and for the operator to enter an input after performing the instruction,
   wherein the first single input and second single input are received to transition to each of the first and second stages, respectively.

2. The medical diagnostic imaging system of claim 1, wherein the first single input and the second single input comprise a same single input; and
   wherein the same single input is received to transition to each stage of the first and second stages.

3. The medical diagnostic imaging system of claim 2, wherein the input device comprises keys on a keyboard; and
   wherein the same single input comprises one of the keys on the keyboard.

4. The medical diagnostic imaging system of claim 3, wherein the same single input comprises a dedicated key.

5. The medical diagnostic imaging system of claim 2, wherein the input device comprises a voice input; and
   wherein the same single input comprises a vocal command.

6. The medical diagnostic imaging system of claim 2, wherein the same single input comprises a footswitch.

7. The medical diagnostic imaging system of claim 2, wherein the protocol controller further is operative to control system parameters of the medical diagnostic imaging system in accordance with the protocol in response to the same single input being activated.

8. The medical diagnostic imaging system of claim 7, wherein the protocol controller controls the system parameters of the medical diagnostic imaging system to guide a user through a pre-defined series of clip acquisitions.

9. The medical diagnostic imaging system of claim 1, wherein the first single innut and the second single input are different.

10. The medical diagnostic imaging system of claim 9, wherein the input device comprises a keyboard with a plurality of keys; and
    wherein the first singe input and the second single input are different keys on the keyboard.

11. The medical diagnostic imaging system of claim 1, wherein the protocol controller automatically labels images generated during the protocol.

12. The medical diagnostic imaging system of claim 11, wherein the automatic labeling of images is based on a mode of a stage of the protocol.

13. The medical diagnostic imaging system of claim 1, further comprising an output device, wherein the protocol controller outputs on the output device a description of a next stage in the protocol.

14. The medical diagnostic imaging system of claim 1, wherein the protocol controller is operative to diverge from the protocol based on user input from the input device.

15. The medical diagnostic imaging system of claim 1, wherein the protocol comprises multiple branches; and
    wherein the protocol controller is operative to transition to one of the multiple branches in response to no more than a single input from the input device.

16. The medical diagnostic imaging system of claim 15, wherein the one of the multiple branches is executed by the protocol controller based on data received by the medical diagnostic imaging system.

17. A medical diagnostic imaging system comprising:
- a storage device storing a protocol for performing a medical diagnostic procedure on the medical diagnostic imaging system, the protocol partitioned into at least two sequential stages, the stages being different from one another;
- an input device having at least one key;
- a protocol controller operative to transition from one stage to a next stage in the protocol in response to no more than a single input from the key of the input device and operative to confrnure the medical diagnostic imagine system for the next stage in the protocol; and
- a display controller operative to display a message prior to the protocol controller configuring the medical diagnostic imagine system for each of the at least two sequential stages in the protocol, the message comprising an instruction for an operator to perform in advance of each of the at least two sequential stages and for the operator to enter an input after performing the instruction,
- wherein the key is dedicated to indicate transitioning to a stage of the protocol during operation of the protocol on the medical diagnostic system, and
- wherein the no more than a single input from the key is received to transition to each stage of the at least two sequential stages.

18. The medical diagnostic imaging system of claim 17, wherein the input device comprises a keyboard with a plurality of keys; and
- wherein the key is a dedicated key to indicate transitioning to a stage of the protocol only during operation of the protocol.

19. The medical diagnostic imaging system of claim 17, wherein the input device comprises a keyboard with a plurality of keys; and
- wherein the key is a dedicated key to indicate transitioning to a stage of the protocol during all operations of the medical diagnostic system.

20. Method for transitioning through a protocol in a medical diagnostic imaging system, the method comprising:
- (i) accessing a protocol for performing a medical diagnostic procedure on the medical diagnostic imaging system, the protocol partitioned into at least a first stage and a second stage, the stages being different from one another;
- (ii) displaying a first message comprising an instruction for an operator to perform in advance of the first stage and to input the first single input;
- (iii) receiving a first single input from an input device in the medical diagnostic imaging system;
- (iv) in response to no more than the first single input, transitioning to the first stage of the protocol and configuring the medical diagnostic imaging system for the first stane;
- (v displaying a second message comprising an instruction for an operator to perform in advance of the second stase and to input the second single input;
- (vi) receiving a second single input from an input device in the medical diagnostic imaging system; and
- (vii) in response to no more than the second single input, transitioning to the second stage of the protocol and configuring the medical diazaostie imaging system for the second stage.

21. The method of claim 20, wherein the first single input in (ii) and the second single input in (iv) are identical.

22. The method of claim 21, wherein the first single input and the second single input are a signal from a key dedicated to transitioning through the protocol.

23. The method of claim 20, after (iii), further comprising controlling system parameters of the medical diagnostic imaging system in accordance with the first stage of the protocol.

* * * * *